US00PP32921P2

(12) United States Plant Patent
Sproul

(10) Patent No.: US PP32,921 P2
(45) Date of Patent: Mar. 30, 2021

(54) CLIMBING ROSE PLANT NAMED 'SPROFIFTH'

(50) Latin Name: *Rosa hybrida*
Varietal Denomination: Sprofifth

(71) Applicant: The Conard-Pyle Company, West Grove, PA (US)

(72) Inventor: James Sproul, Bakersfield, CA (US)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 16/602,930

(22) Filed: Dec. 30, 2019

(51) Int. Cl.
*A01H 5/02* (2018.01)
*A01H 6/74* (2018.01)

(52) U.S. Cl.
USPC ..... Plt./109
CPC ..... *A01H 6/749* (2018.05)

(58) Field of Classification Search
USPC ..... Plt./115, 109
CPC ..... A01H 5/0222
See application file for complete search history.

(56) References Cited

U.S. PATENT DOCUMENTS

| | | | |
|---|---|---|---|
| PP11,518 | P | 9/2000 | Carruth |
| PP19,310 | P2 | 10/2008 | Radler |
| PP23,549 | P3 | 4/2013 | Sproul |

*Primary Examiner* — Kent L Bell
(74) *Attorney, Agent, or Firm* — Panitch Schwarze Belisario & Nadel LLP; Stephany G. Small; Travis W. Bliss

(57) ABSTRACT

A new and distinct variety of climbing rose plant, herein referred to by its cultivar name, 'Sprofifth', is provided which forms abundantly on a substantially continuous basis attractive, cup-like shaped red colored blossoms with dark red stripes. Attractive glossy, dark green foliage is formed, which contrasts beautifully with the blossoms. The growth habit is very bushy and climbing. The new variety is well suited for providing attractive ornamentation in the landscape.

1 Drawing Sheet

Botanical/commercial classification: Latin name—*Rosa hybrida.*

Varietal denomination—'Sprofifth'.

SUMMARY OF THE INVENTION

The new variety of *Rosa hybrida* climbing rose plant was created during April of 2010 in Bakersfield, Calif., U.S.A., by artificial pollination wherein two parents were crossed which previously had been studied in the hope that they would contribute the desired characteristics. The female parent (i.e., the seed parent) was the 'WEKroalt' variety (U.S. Plant Pat. No. 11,518). The male parent (i.e., the pollen parent) was the 'Sprothrive' variety (U.S. Plant Pat. No. 23,549).

The parentage of the new variety can be summarized as follows:

'WEKroalt' x 'Sprothrive'

The seeds resulting from the above pollination were sown and small plants were obtained which were physically and biologically different from each other. Selective study resulted in the identification of a single plant of the new variety.

It was found that the new variety of rose plant of the present invention possesses the following combination of characteristics:

(a) forms attractive, cup-like shaped, red colored blossoms with dark red stripes,
(b) displays a very bushy and climbing growth habit,
(c) forms vigorous vegetation, and (d) provides attractive ornamental glossy, dark green foliage.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'WEKroalt' variety (i.e., the seed parent) grows shorter and displays larger blossom compared to the new variety. In addition, the 'Sprothrive' variety (i.e., the pollen parent) provides solid dark bright red colored flowers and a round and bushy growth habit, whereas the new variety displays striped red colored flowers and a climbing growth habit. Moreover, the new variety can be readily distinguished from other similar non-parental varieties. For example, the 'Radwin' variety (U.S. Plant Pat. No. 19,310) displays solid red colored blossoms, whereas the new variety displays striped red colored flowers.

The new variety has been found to undergo asexual propagation at Wasco, Calif. and at Cochranville, Pa. by a number of routes, including vegetative cuttings. Asexual propagation by vegetative cuttings at Wasco, Calif. and at Cochranville, Pa. has shown that the characteristics of the new variety are stable and are strictly transmissible by such asexual propagation from one generation to another. Accord ingly, the new variety undergoes asexual propagation in a true-to-type manner.

The new variety has been named 'Sprofifth'.

The new variety was first offered for sale on March, 2019 by the inventor or another who obtained the new variety directly or indirectly from the inventor and the first sale was on Apr. 30, 2019 by the inventor or another who obtained the new variety directly or indirectly from the inventor.

BRIEF DESCRIPTION OF THE PHOTOGRAPH

The accompanying photograph of FIG. 1 shows as nearly true as it is reasonably possible to make the same, in a color illustration of this character, a typical specimen of the new variety. The rose plant of the new variety was approximately three years of age and was observed during May 2019 while growing on its own roots and growing outdoors in a three-gallon container at Cochranville, Pa., U.S.A.

FIG. 1—illustrates a specimen a plant with open blossoms.

DETAILED BOTANICAL DESCRIPTION

The chart used in the identification of the colors is that of The Royal Horticultural Society (R.H.S. Colour Chart, 2015 edition), London, England. The terminology which precedes reference to the chart has been added to indicate the corresponding color in more common terms. The description is based on the observation of three-year-old specimens of the new variety during May while growing on their own roots in a three-gallon container at Cochranville, Pa., U.S.A.

Commercial classication: Climbing Rose Plant.

Plant:

*Habit.*—Very bushy, upright, and climbing.

*Height.*—Approximately 60.0 cm on average from the top of the soil plane.

*Width.*—Approximately 60.0 cm on average.

Branches:

*Color.*—Young stems: commonly near Green Group 143A. — old wood: commonly near Green Group 137B.

*Length.*—Main stems: approximately 60.0 cm on average. — secondary stems: approximately 20.0 cm on average.

*Diameter.*—Main stems: approximately 5.0 mm on average. — secondary stems: commonly 3.0 mm to 4.0 mm on average.

*Thorns.*—Young thorns: amount is moderate, length is approximately 8.0 mm on average, width is approximately 4.0 mm on average at point of attachment, and color is commonly near Greyed-Orange Group 166B. — old thorns: amount is moderate, length is approximately 1.0 cm on average, width is approximately 5.0 mm on average, and color is commonly near Grey Group 201A.

Foliage:

*General appearance.*—Dark green with a glossy aspect.

*Young foliage.*—Upper surface color: commonly near Yellow-Green Group 146A with indistinguishable venation. — under surface color: commonly near Yellow-Green Group 146B with indistinguishable venation.

*Old foliage.*—Upper surface color: commonly near Green Group 137A with indistinguishable venation. — under surface color: commonly near Green Group 137B with indistinguishable venation.

*Petiole.*—Upper surface: color is commonly near Green Group 137A and texture is smooth. — under surface: color is commonly near Green Group 137C and texture is glandular with some small prickles. — length: approximately 3.0 cm on average. — diameter: approximately 2.0 mm on average.

*Rachis.*—Color of upper surface: commonly near Green Group 137A. — color of under surface: commonly near Green Group 137C. — length: approximately 5.0 cm on average. — diameter: approximately 2.0 mm on average.

*Stipules.*—Margin: entire to erose. — length: approximately 2.0 cm on average. — width: approximately 1.0 cm on average. — color of upper surface: commonly near Green Group 137B. — color of lower surface: commonly near Green Group 137C.

5-*Leaflet leaf.*—Length: approximately 9.0 cm on average. — width: approximately 7.0 cm on average.

Leaflets:

*Number of leaflets.*—3, 5, and 7.

*Shape.*—Ovate; apex is rounded; and base is rounded.

*Leaflet margin.*—Serrate.

*Texture.*—Upper and under surfaces is smooth.

*Venation.*—Pattern: reticulate. — color (both surfaces): indistinguishable to the leaflet color.

*Terminal leaflet.*—Length: approximately 4.0 cm on average. — width: approximately 3.5 cm on average.

*Lower leaflet.*—Length: approximately 3.0 cm on average. — width: approximately 2.5 cm on average.

Inflorescence:

*Number of flowers.*—Generally about 20 blooms on average on a plant at once.

*Number of blooms per stem.*—Generally between 3 and 5 blooms per stem on average.

*Peduncle.*—Length: approximately 3.0 cm on average. — diameter: approximately 3.0 mm on average. — surface texture: moderately covered in short, flexible thorns that measure less than 1.0 mm in length. — color: commonly near Green Group 137C.

*Sepals.*—Number: commonly 5. — shape: lanceolate; apex is acute to aristate. — length: approximately 2.0 cm on average. — width: approximately 9.0 mm on average. — margin: entire with extensions on two or three sepals measuring approximately 5.0 mm in length on average and 1.0 mm in width on average. — upper surface color and texture: commonly near Yellow-Green Group 144A; covered in short pubescence. — under surface color and texture: commonly near Yellow-Green Group 144B; puberulent.

*Bud.*—Shape: ovoid. — length: approximately 2.0 cm on average. — width: approximately 1.5 cm on average. — color when opening: commonly between Red-Purple Group 59A and Red-Purple Group 59B with some coloring of near Red-Purple Group 63C.

*Flower.*—Diameter: approximately 6.5 cm on average. — height: approximately 2.0 cm on average. — duration: flower is on the plant approximately 5 to 7 days. — shape: cuplike. — form: semi-double. — number of petals under normal conditions: approximately 10 petals on average. — shape of the petal: overall: broadly obovate. apex:

round. base: rounded to cuneate. — petal length: approximately 3.0 cm on average. — petal width: approximately 3.0 cm on average. — petal margin: entire with a moderate undulation. — petal texture (both surfaces): glabrous. — petal drop: very good. — petaloids: none present. — fragrance: very slight. — petal color when first and fully open: upper surface: commonly near Red Group 53C with striping of near Red Group N45A and a basal spot of commonly near Yellow Group 4B. under surface: commonly near Red Group 50D with striping of near Red Group 53C and a basal spot of commonly near Yellow Group 4C. — petal color at end of blooming: upper surface: commonly near Red-Purple Group 61B with striping of near Red-Purple Group 59A and a basal spot of near Yellow Group 4D. under surface: commonly near Red-Purple Group 63D with striping of near Red-Purple Group 59C and a basal spot of near Yellow Group 11D.

*Receptacle.*—Achenes stand on the bottom and wall. — color: commonly near Yellow-Green Group 144A. — diameter: approximately 7.0 mm on average. — depth: approximately 9.0 mm on average. — surface texture: smooth. — shape: round.

*Stamen.*—Number is approximately 115 on average. — anthers: number is approximately 115 on average; color is commonly near Yellow-Orange Group 22A; length is less than 1.0 mm on average; and shape is oval. — filaments: length is approximately 7.0 mm on average and color is commonly near Yellow Group 9A.

*Pistils.*—Arrangement is separate and free; number is approximately 30 on average. — styles: length is approximately 3.0 mm on average and color is commonly near Red-Purple Group 63A. — stigmas: diameter is typically less than 1.0 mm and color is commonly near Yellow Group 13B.

*Ovary.*—Length is approximately 3.0 mm on average, width is approximately 1.0 mm on average, and color is commonly near Yellow-White Group 158B.

*Pollen.*—Color is commonly near Orange Group 26B and a sparse amount is present.

*Hips.*—None observed.

Development:

*Vegetation.*—Glossy, dark green, vigorous and strong.

*Blooming.*—Abundant and substantially continuous from late May to November in Southeastern Pennsylvania.

*Resistance to disease.*—Very good resistance for black spot (*Diplocarpon rosae*) and powdery mildew (*Sphaerotheca pannosa*).

*Pest resistance/susceptibility.*—None observed to date.

*Hardiness.*—Hardy to USDA Zone 5.

The new 'Sprofifth' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of Climbing Rose plant characterized by the following combination of characteristics:

(a) forms attractive, cup-like shaped, red colored blossoms with dark red stripes, (b) displays a very bushy and climbing growth habit, (c) forms vigorous vegetation, and (d) provides attractive ornamental glossy, dark green foliage;

substantially as herein shown and described.

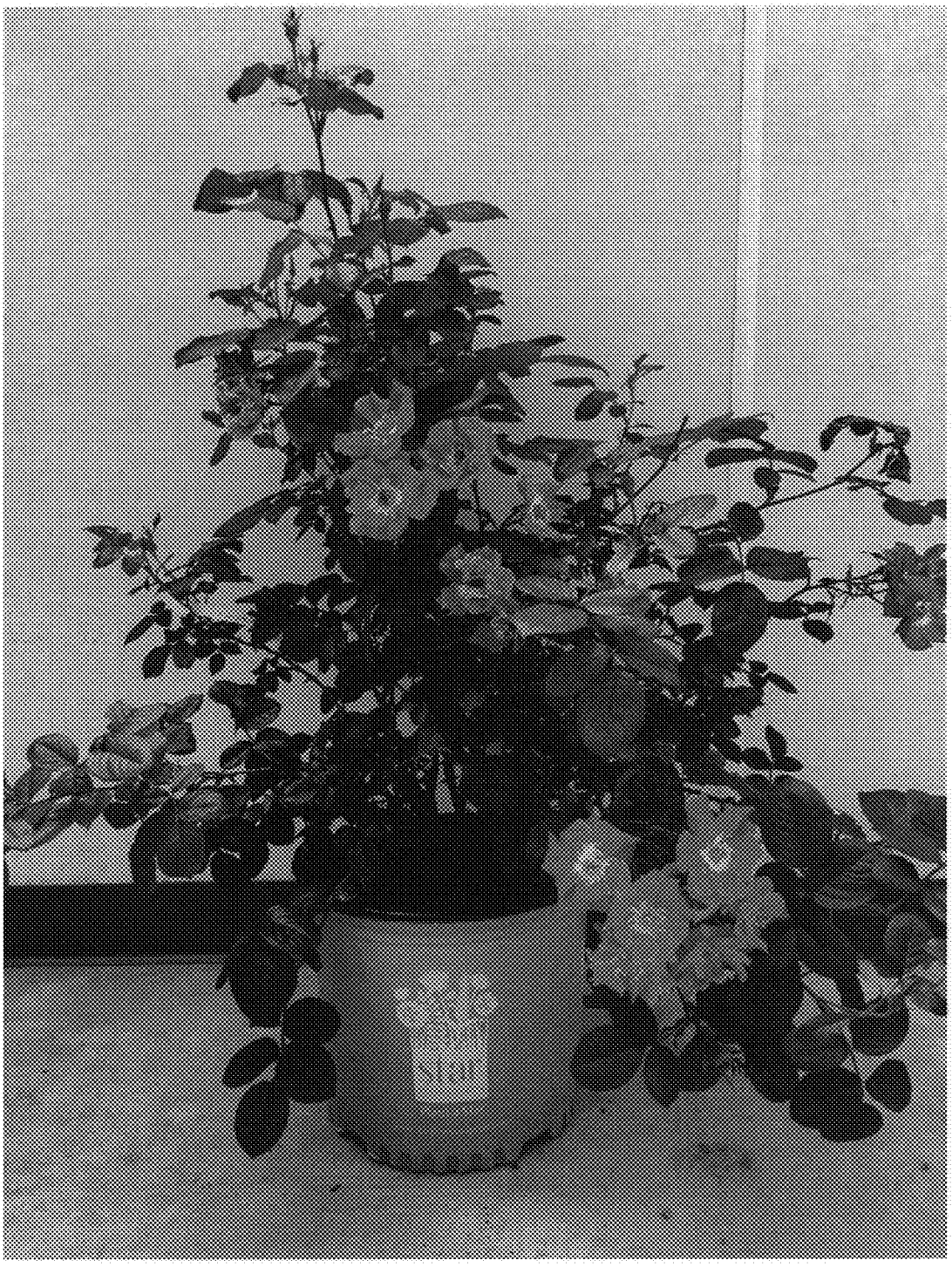

* * * * *